United States Patent [19]
Burke

[11] 3,957,923
[45] May 18, 1976

[54] ALKYL AND HALOALKYL N,N'-DIALKYL-N-METHYLOLPHOSPHORODIAMIDATES

[75] Inventor: Patrick Michael Burke, Wilmington, Del.

[73] Assignee: E. I. Du Pont de Nemours & Company, Wilmington, Del.

[22] Filed: Feb. 18, 1975

[21] Appl. No.: 550,619

Related U.S. Application Data

[60] Division of Ser. No. 373,144, June 25, 1973, Pat. No. 3,897,522, which is a continuation-in-part of Ser. No. 261,812, June 12, 1972, abandoned.

[52] U.S. Cl. ............................... 260/936; 428/276; 428/921; 427/394

[51] Int. Cl.$^2$ ..................... C07F 9/24; C06C 27/00
[58] Field of Search .................. 260/936

[56] References Cited
UNITED STATES PATENTS

| | | | |
|---|---|---|---|
| 3,463,813 | 8/1969 | Dickerson | 260/936 X |
| 3,522,303 | 8/1970 | Ulrich | 260/936 X |

Primary Examiner—Anton H. Sutto

[57] ABSTRACT

Alkyl and haloalkyl N,N'-dialkyl-N-methylolphosphorodiamidates, for example, methyl N,N'-dimethyl-N,N'-dimethylolphosphorodiamidate, useful for rendering combustible cellulosic materials flame resistant.

4 Claims, No Drawings

ALKYL AND HALOALKYL N,N'-DIALKYL-N-METHYLELPHOSPHORODIAMIDATES

CROSS-REFERENCE TO RELATED APPLICATION

This is a division of application Ser. No. 373,144 filed June 25, 1973, now U.S. Pat. No. 3,897,522, which is a continuation-in-part of application Ser. No. 261,812 filed June 12, 1972 and abandoned July 2, 1973.

BACKGROUND OF THE INVENTION

1. Field of the Invention

This invention relates to alkyl and haloalkyl N,N'-dialkyl-N-methylolphosphorodiamidates.

2. Description of the Prior Art

Phosphorus-containing compounds are well known for their ability to impart flame resistance to fabrics. Many of such prior art compounds may be undesirable as flame retardants for fabrics because they stiffen the fabric, because of their volatility which leads to their loss, at least partially, during any curing operation, because of their toxicity, because they must be employed in large quantities to impart any significant flame resistance to the fabric, or because they are not fast to laundering. Known flame retardants for fabrics include phosphorodiamidates. Such materials usually are employed in combination with aminoplast resin precondensates to achieve durability or fastness to laundering. If the amount of aminoplast required is high, excessive and intolerable stiffening of the fabric may result.

British Pat. No. 799,606 discloses that textile fabrics can be made flame resistant with N-methylol derivatives of alkyl or aryl esters of phosphorodiamidic acid, the alkyl or aryl group optionally being substituted with, for example, halogen. Preferably, the diamidic acid derivative is employed in combination with an amino-aldehyde resin. Such diamidic acid compounds may be undesirable because they impart objectionable stiffness to the fabric, because they cannot be made up into storage stable solutions, because the washfastness of the flame resistance imparted to the fabric decreases with increasing age of the solution before application, or because the flame resistance imparted to the fabric is not durable to home bleaching. Moreover, such diamidates may be undesirably expensive, in pure form, if they are prepared from a phosphoryl chloride, an alcohol and ammonia, yielding the difficulty separable ammonium chloride as a by-product.

U.S. Pat. No. 2,828,228 discloses the use of alkyl and haloalkyl phosphorodiamidates and monoamidates, with or without N-alkyl substituents, in combination with a methylolmelamine for rendering cellulosic fibers flame resistant. Such flame retardants may impart undesirable stiffness to the cellulosic fibers. Similar amidates are disclosed in British Pat. No. 790,663 for imparting flame resistance to cellulosic materials.

British Pat. No. 1,222,885 discloses as flame retardants for cellulosic materials, compounds or combinations of compounds which contain nitrogen and phosphorus. It further discloses that fabrics treated with such a compound or combination of compounds have a good degree of flame retardance if the nitrogen content is equal to or greater than 6% minus 4 times the phosphorus content and, preferably, is at least 2.5 times the phosphorus content, with the preferred amounts of nitrogen and phosphorus totaling at least 3.5%, based on the weight of fabric. Exemplary of compounds containing both nitrogen and phosphorus are phosphorodiamidates having the formula

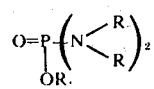

wherein R can be substituted or unsubstituted $C_{1-6}$ alkyl.

U.S. Pat. No. 2,832,745 discloses the use of phosphorodiamidates in combination with an adduct of a polymerizable phosphate ester and a polymethylol amide, azine or azole for imparting flame resistance to flammable materials, and U.S. Pat. No. 2,971,929 discloses a five-component mixture for imparting flame resistance and water repellency to combustible materials, which mixture can include an alkyl N,N'-dialkyl-phosphorodiamidate.

German Pat. No. 1,009,629 discloses flame retarding phosphorus compounds which are obtained by treating phosphoric triamide with formaldehyde and methanol. The product, which includes phosphorus esters and hexamethylenetetramine, appears to lack durability to laundering.

SUMMARY OF THE INVENTION

It is an object of this invention to provide compositions which are highly effective in imparting flame resistance to combustible cellulosic materials. Another object is to provide phosphorus-containing compositions which impart flame resistance to such cellulosic materials. Still another object is to provide flame resistant cellulosic materials. A further object is to provide such flame resistant materials which are durable to laundering and bleaching operations. Another object is to provide compositions which impart flame resistance to combustible cellulosic fabrics without deleteriously affecting the physical appearance and hand of the fabric. A still further object is to provide phosphorus-containing compounds which can be formulated into storage stable liquids which are useful in imparting flame resistance to combustible cellulosic materials.

The above objects are fulfilled by the present invention which, in summary, resides in alkyl N,N'-dialkyl-N-methylolphosphorodiamidates having the formula

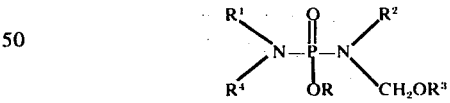

wherein R is $C_{1-5}$ alkyl having 0–3 substituents selected from chloro and bromo, each of $R^1$ and $R^2$ when taken singly is selected from $C_{1-3}$ alkyl and $C_{1-3}$ chloro- or bromoalkyl, $R^3$ is H or $C_{1-4}$ alkyl, $R^4$ is H or $CH_2OR^5$ wherein $R^5$ is H or $C_{1-4}$ alkyl and $R^1$ and $R^2$ when taken conjointly is $C_{2-5}$ alkylene, provided that all carbon atoms alpha to the amide nitrogen and ester oxygen atoms are free of halo substituents. The invention includes storage stable solutions which can be formulated from the aforesaid phosphorodiamidates, the process of applying such solutions, optionally containing aminoplast resin intermediates, to combustible cellulosic materials, such as fabrics, and the durably flame resistant cellulosic materials which are produced by such process.

DETAILED DESCRIPTION OF THE INVENTION

This invention is based upon the discovery that the alkyl and haloalkyl N,N-'-dialkyl-N-methylolophosphorodiamidates as defined above are more effective than prior art compounds of similar structure in imparting durable flame resistance to combustible cellulosic materials, such as fabrics, and that fabrics can be treated with such compounds without substantial alteration of their physical appearance, softness or hand. The increased effectiveness of the compounds of this invention is believed to be due, at least partially, to their lower volatility at the elevated temperatures encountered in the curing step conventionally employed in fabric treating operations.

In the phosphorodiamidates of this invention as already defined, R can be selected from N-pentyl, isopentyl, neopentyl, 2-methylbutyl, 3-methylbutyl, n-butyl, isobutyl, tertiary butyl, n-propyl, isopropyl, ethyl and methyl radicals, the latter two being preferred. It also can be selected from $C_2$ to $C_5$ haloalkyl radicals having 1 to 3 halogen atoms selected from chlorine and bromine on carbon atoms in the $\beta$ and higher relation to the attached oxygen, that is, on carbon atoms other than the one alpha to the ester oxygen atom. Preferred haloalkyl radicals have 2 to 5 carbon atoms and 1 to 3 halogen atoms on carbon atoms which are in at least the $\beta$-position (that is, $\beta$-and farther removed) to the ester oxygen atom. Typical haloalkyl radicals include 2,2-bis(bromomethyl)-3-bromopropyl, 1-(bromomethyl)-2-methyl-2,3-dibromopropyl, 1-(bromomethyl)-1-methyl-2,3-dibromopropyl, 2-(bromomethyl)-2-methylpropyl, 1-(bromomethyl)-2,3-dibromopropyl, 1-bromomethyl-2-bromopropyl, 1-methyl-2,3-dibromopropyl, 2-chlorobutyl, 2-bromobutyl, 3-chloro-2-butyl, 3-bromo-2-butyl, 1-chloro-2-butyl, 1-bromo-2-butyl, 4-chloro-2-butyl, 4-chlorobutyl, 4-bromobutyl, 2,3-dichloro-2-methylpropyl, 2-bromo-3-chloro-2-methylpropyl, 1,3-dichloro-2-methyl-2-propyl, 1-chloro-3-bromo-2-methyl-2-propyl, 1,3,4-trichloro-2-butyl, 1,4-dichloro-3-bromo-2-butyl, 2-chloroethyl, 2-bromoethyl, 2,2,2-trichloroethyl, 2-chloropropyl, 2-bromopropyl, 3-chloropropyl, 3-bromopropyl, 2,3-dichloropropyl, 2,3-dibromopropyl, 2-chloro-3-bromopropyl, 2-bromo-3-chloropropyl, 1,3-dichloro-2-propyl, 1,3-dibromo-2-propyl and 1-chloro-3-bromo-2-propyl. The most preferred haloalkyl radicals have 5 carbon atoms and 3 bromine atoms, such as 2,2-bis(bromomethyl)-3-bromopropyl, 1-bromomethyl-2,3-dibromopropyl and 1-(bromomethyl)-1methyl-2,3dibromopropyl.

$R^1$ and $R^2$ in the above formula can be the same or different, preferably the same, and each is selected from methyl, ethyl, n-propyl and isopropyl groups, the first two being preferred. These alkyl groups can bear a chlorine or bromine atom in the $\beta$ or $\gamma$ relation to the attached nitrogen atom, that is, the halogen atom cannot be attached to the carbon atom which is alpha to the amide nitrogen atom. Examples of haloalkyl groups include 1-bromo-2-propyl, 1-chloro-2-propyl, 2-bromomethyl and, preferably, 2-chloroethyl.

$R^1$ and $R^2$ can together (conjointly) constitute an alkylene radical of 2 to 5 carbon atoms wherein the two free valences are in a 1,2- or 1,3-relation to each other, as in 1,2-ethylene, 1,2-propylene, 1,3-propylene, 1,3-butylene, 1,3-pentylene, 2,4-butylene, 2-methyl-2,4-butylene and 2,4-pentylene. The 1,3-propylene diradical is a preferred combination of $R^1$ and $R^2$.

In the preferred compounds of this invention $R^4$ is $CH_2OR^5$. In such event, $R^3$ and $R^5$ can be the same or different although they preferably will be the same. $R^3$ and $R^5$ alkyl groups can be selected from tertiary butyl, secondary butyl, n-butyl, isopropyl, n-propyl, ethyl and methyl, the latter two being preferred.

Typical phosphorodiamidates of this invention include those of the above formula wherein the various R groups are as set forth in Table I. Compounds 8 to 20 and 27 to 33 in the table are preferred and, of these, 18 to 20 and 31 to 33 are especially useful.

TABLE I

| | R | $R^1$ | $R^2$ | $R^3$ | $R^4$ |
|---|---|---|---|---|---|
| 1. | 1,4-dichloro-3-bromo-2-butyl | 1-bromo-2-propyl | 1-bromo-2-propyl | H | $CH_2OH$ |
| 2. | 1,3,4-trichloro-2-butyl | 1-chloro-2-propyl | 1-chloro-2-propyl | H | $CH_2OH$ |
| 3. | 2,3-dibromopropyl | methyl | 2-bromoethyl | H | H |
| 4. | 2,3-dibromopropyl | 2-bromoethyl | methyl | H | H |
| 5. | 2-chloropropyl | methyl | 2-chloropropyl | H | H |
| 6. | 2-chloropropyl | 2-chloropropyl | methyl | H | H |
| 7. | 1,3-dichloro-2-propyl | 2-chloroethyl | 2-chloroethyl | H | H |
| 8. | 2,3-dichloropropyl | 2-chloroethyl | methyl | H | $CH_2OH$ |
| 9. | 2-chloroethyl | ethyl | methyl | H | $CH_2OH$ |
| 10. | ethyl | methyl | methyl | H | H |
| 11. | methyl | methyl | methyl | H | $CH_2OH$ |
| 12. | 2-chloroethyl | methyl | methyl | H | H |
| 13. | 2-chloroethyl | ethyl | ethyl | H | $CH_2OH$ |
| 14. | 2-chloroethyl | trimethylene | | H | $CH_2OH$ |
| 15. | 2-chloroethyl | 2-chloroethyl | 2-chloroethyl | H | $CH_2OH$ |
| 16. | 2-chloroethyl | ethyl | ethyl | H | isobutoxymethyl |
| 17. | 1,3-dichloro-2-propyl | 2-chloroethyl | 2-chloroethyl | H | $CH_2OH$ |
| 18. | 2-chloroethyl | methyl | methyl | $CH_3$ | $CH_2OCH_3$ |
| 19. | 2-chloroethyl | methyl | methyl | H | $CH_2OH$ |
| 20. | 2,3-dibromopropyl | methyl | methyl | H | $CH_2OH$ |
| 21. | 1-methyl-2,3-dibromopropyl | methyl | methyl | H | H |
| 22. | 1-methyl-2,3-dibromopropyl | methyl | methyl | H | $CH_2OH$ |
| 23. | 1-(bromomethyl)-2-bromopropyl | methyl | methyl | H | H |
| 24. | 1-(bromomethyl)-2-bromopropyl | methyl | methyl | H | $CH_2OH$ |
| 25. | 1-(bromomethyl)-2,3-dibromopropyl | methyl | methyl | H | H |
| 26. | 1-(bromomethyl)-2,3-dibromopropyl | methyl | methyl | H | $CH_2OH$ |
| 27. | 1-(bromomethyl)-1-methyl-2,3-dibromopropyl | methyl | methyl | H | H |
| 28. | 1-(bromomethyl)-1-methyl-2,3-dibromopropyl | methyl | methyl | H | $CH_2OH$ |
| 29. | 1-(bromomethyl)-2-methyl-2,3-dibromopropyl | methyl | methyl | H | H |
| 30. | 1-(bromomethyl)-2-methyl-2,3-dibromopropyl | methyl | methyl | H | $CH_2OH$ |
| 31. | 2,2-bis(bromomethyl)-3-bromopropyl | methyl | methyl | H | H |
| 32. | 2,2-bis(bromomethyl)-3-bromopropyl | methyl | methyl | H | $CH_2OH$ |

TABLE I-continued

| | R | R¹ | R² | R³ | R⁴ |
|---|---|---|---|---|---|
| 33. | 2,2-bis(bromomethyl)-3-bromopropyl | | trimethylene | H | CH$_2$OH |

The hydroxymethyl compounds of this invention can be made by reacting the appropriate non-methylolated phosphorodiamidate, obtainable by known procedures, and formaldehyde in a solvent for the reaction product, under acidic, neutral or basic conditions, preferably basic conditions. The solvent may be aqueous, nonaqueous or a mixture of aqueous and nonaqueous. For economic reasons it is preferably aqueous, with water serving as the essential solvent or as an extender of an organic solvent for the reaction product. A convenient form of formaldehyde for use in the methylolation is 37% aqueous formaldehyde. When the reaction is carried out under basic conditions, a convenient pH is 8–12, preferably 9–11. Any soluble alkalizing material can provide the desired basic pH, such as sodium silicate, sodium carbonate, trisodium phosphate and the like, but sodium hydroxide or potassium hydroxide is preferred. The reaction is carried out at 0°–30°C., preferably 10°–20°C.

Progress of the reaction can be followed by periodic broad band proton decoupled P-31 nuclear magnetic resonance (NMR) spectrum analyses of the reaction mixture using 85% phosphoric acid as the external standard. The noncyclic phosphorodiamidate starting materials have a characteristic band or multiplet of peaks in the range −18 to −22 ppm. relative to the standard; as the methylol compound is formed, its peaks in the NMR spectrum shaft toward the standard and show a shifted band of peaks centered in the range −15 to −19 ppm.

The ppm. values reported herein are given as negative values to indicate that the bands are shifted in a negative direction from the bands in 85% phosphoric acid which is the standard.

N,N′-Alkylenephosphorodiamidates in a suitable solvent have characteristic peaks in the range −15.5 to −16.0 ppm.; the monomethylol derivatives show shifted bands of peaks centered at about −13.9 to −14.9 ppm.; the dimethylol derivatives, at −12.2 to −13.2 ppm.

Typically, the P-31 NMR spectrum of solutions of 2-chloroethyl N,N′-dimethylphosphorodiamidate in water, methanol or chloroform changes from a peak at −21±1 ppm. (characteristic of the unmethylolated material in such solvents) to peaks in the range −19.4 to −16.1 ppm. (characteristic of the mono- and dimethylol derivatives). The P-31 NMR spectrum of solutions of 3-chloropropyl N,N′-dimethylphosphorodiamidate changes from a peak at −19.1 ppm. to a multiplet of peaks centered at −16.7 ppm. (characteristic of the dimethylol derivative). The P-31 NMR spectrum of solutions of 2,2,2-trichloroethyl N,N′-dimethylphosphorodiamidate changes from a peak a −19.0 ppm. to a multiplet of peaks centered at −16.0 ppm. (characteristic of the dimethylol derivative). The P-31 NMR spectrum of solutions of 2,2-bis(bromomethyl)-3-bromopropyl N,N′-dimethylphosphorodiamidate changes from a peak at −19.6±0.1 ppm. to peaks at −18.2 and −17.6 ppm. characterizing the monomethylol derivative and to peaks at −16.3, −16.0 and −15.5 ppm. characterizing the dimethylol derivative. Aqueous solutions of 2-chloroethyl N,N′-trimethylenephosphorodiamidate having a P-31 NMR spectrum with a peak at −15.8 ppm.; this peak shifts to a band centered at about −14.4 ppm. for the monomethylol derivative and to about −12.7 ppm. for the dimethylol derivative. When the shifted band or multiplet of peaks becomes constant, the methylolation is complete.

The alkoxymethyl compounds of this invention can be made directly from the appropriate unmethylated phosphorodiamidate, obtainable by known means, and a chloromethyl ether ClCH$_2$OR³ (R³ previously defined) in an alkaline medium, for example, at a pH of 8–12, preferably 9–11. The alkoxymethyl compounds also can be made by etherifying the previously described hydroxymethyl compounds with an alcohol R³OH (R³ previously defined) in an acidic alcoholic medium, for example, at a pH of 1–5, preferably 2–3. The formation of the alkoxymethyl compounds also can be followed by periodically monitoring the P-31 NMR spectrum during the reaction.

As indicated above, the phosphorodiamidate intermediates for making the compounds of this invention can be produced by known methods. For example, the ester portion of the compound can be provided by reacting an alkanol or a halogenated alkanol ROH (R previously defined) with a phosphoryl halide by a procedure such as disclosed in U.S. Pat. No. 2,716,657 or by G. M. Kosolapoff in "Organophosphorus Compounds", John wiley and Company (1950), or by reacting the phosphoryl halide and a 1,2-alkyleneimine employing a procedure such as disclosed by N.P. Grechkin in Izvest. Akad. Nauk S.S.S.R., Otdel, Khim. Nauk 1956, 538–43 or in Textile Research Journal, page 669, August, 1970. The use of phosphoryl halide in molar excess over the hydroxy compound favors monoesterification. The ester portion of the compound also can be provided by reacting cyclic ethers, optionally having appropriately positioned chlorine or bromine substituents, and phosphoryl halides by a known procedure such as disclosed in U.S. Pat. Nos. 1,936,985; 2,157,164; 2,610,978; and 2,716,657 or by Kosolapoff, supra, page 230. Cyclic ethers which are useful in such a reaction include 1,2-expoxides, such as ethylene oxide, propylene oxide, epichlorohydrin, epibromohydrin, 1,2- and 2,3-butylene oxides, 2-methylpropylene oxide and 1,4-dichloro-2,3-butylene oxide; 1,3-epoxides, such as 1,3-propylene oxide, 1,3-butylene oxide, 4-chloro-1,3-butylene oxide and 2-chloro-1,3-propylene oxide; and 1,4-cyclic oxides, such as tetrahydrofuran and its halogenated derivatives.

The phosphorus esters obtained as recited immediately above can be reacted with a primary amine to provide the diamide moieties. Such procedures also are well known, for example, as disclosed by Kosolapoff, a supra, page 279, by Caven in the Journal of the Chemical Society 81, 1362 (1902) or by Michaelis in Annalen 326, 129 (1903).

The aforesaid procedures can be employed to produce symmetrical or unsymmetrical diamidates.

The compounds of this invention can be used directly as prepared (in the reaction medium), they can be isolated and subsequently placed in solution or they can be emulsified in aqueous media for application to a combustible cellulosic material. As initially prepared, based upon NMR evaluation and their effectiveness in imparting flame resistance, the compounds are stable in the reaction medium for several months. The isolated compounds are stable indefinitely. Isolation can be carried out by stripping off the solvent from the reaction medium. The compounds, viscous oils to soft solids, can be redissolved or emulsified in water and/or organic, preferably water soluble, solvents. A first class of water soluble organic solvents includes such solvents in which the compounds are soluble and which have boiling points above room temperature up to about 170°C., preferably up to about 115°C., for example, monohydric aliphatic alcohols of 1 to 4 carbon atoms, such as methyl, ethyl, isopropyl and butyl alcohols, ethylene glycol, monoethers of dihydric alcohols, such as methyl Cellosolve and ethyl Cellosolve, tetrahydrofuran, m- and p-dioxane, acetone, methyl ethyl ketone, dimethyl sulfoxide, dimethylacetamide and dimethylformamide. A second class of water soluble solvents includes water soluble poly(oxyalkylene) ethers having molecular weights of 200 to 1,000, for example, poly(oxyethylene) ethers, preferably of molecular weights 250 to 450. Such solvents serve as useful carrier solvents for applying the phosphorodiamidates to the combustible substrate. Preferably, the carrier solvent should be capable of swelling the combustible cellulosic material being rendered flame resistant to facilitate penetration of the cellulose by the phosphorodiamidate. Preferred organic solvents of the first class include methyl, ethyl and isopropyl alcohols and dimethylformamide. When the organic solvent is not completely misible with water, it is convenient to incorporate a dispersing agent and emulsify the phosphorodiamidate, solvent and water. The dispersing agent should function in alkaline, neutral and weakly acidic aqueous media. Typical agents are alkali salts of sulfated straight chain $C_8$ to $C_{20}$ fatty alcohols. The agents can be used in concentrations of 0.1 to 5%, preferably 0.2 to 2% by weight.

The flame resistance imparted to combustible cellulosic materials by a compound of this invention is made durable to laundering by fixing or curing the compound after it has been applied, as a solution or emulsion thereof, to the substrate. Curing is carried out for a sufficient time and at such a temperature that the compound of the invention is insolubilized in the substrate. Representative of such an operation, the substrate which is impregnated with a solution of a compound of this invention is dried at 20°–115°C. Curing is effected at 150°–190°C., preferably at 160°–180°C., in the presence of an acidic curing catalyst for 2–10 minutes, preferably 2–4 minutes. Because of the nonvolatility of the compounds of this invention, drying and curing can be carried out readily in one step if desired. The catalyst usually is dissolved in the solution of phosphorodiamidate before the solution is applied to the material being treated. The amount of catalyst employed usually is 0.5–5 weight %, preferably 1–2.5%, based on the weight of solution.

Catalysts suitable for use in curing or fixation are those which are acidic and are not lost by volatilization at fixing temperatures. Typical catalysts include protonic and Lewis acids which include organic acids, such as oxalic acid, tartaric acid, glycolic acid, lactic acid, succinic acid, citric acid and malic acid, as well as inorganic acids, such as the ammonium salts of hydrochloric acid, phosphoric acid and sulfuric acid, and acid salts, such as zinc fluoborate, zinc chloride, zinc nitrate, magnesium chloride and magnesium nitrate. Other useful catalysts are the ammonium salts of the above-mentioned organic acids and amine salts, such as the hydrochlorides of 2-amino-2-methyl-1-propanol and tris(2-hydroxyethyl)amine. The preferred catalysts include ammonium chloride and 2-amino-2-methyl-1-propanol hydrochloride.

When the phosphorodiamidates of this invention are used to impart a significant degree of flame resistance to combustible cellulosic materials, they usually are applied in combination with other agents conventional in the art for enhancing flame resistance and for improving the durability of the effect. The phosphorodiamidates of this invention are applied to the cellulosic material, for example, fibers, in the form of liquid compositions or solutions to achieve good penetration into the cellulosic material. The liquid composition generally comprises the phosphorodiamidate, a curring catalyst, an aminoplast resin precursor, more fully described below, and a carrier medium which can wet, penetrate and swell the cellulose and which does not interfere with fixation of the phosphorodiamidate. Other adjuvants, such as dispersing agents and nonionic wetting agents, may also be advantageously incorporated into the treating solution.

The liquid composition generally contains 5–80 weight %, preferably 20–60% of active ingredient. The active ingredient can be either a phosphorodiamidate of this invention or, preferably, a combination of such phosphorodiamidate with 0.25–0.5 its weight of an aminoplast resin precursor, that is, the weight of aminoplast resin precursor is 25–50% of the weight of the phosphorodiamidate.

Aminoplast resin precursors or intermediates useful in combination are water soluble compounds containing at least two moles of condensed formaldehyde, for example, as N-hydroxymethyl groups or $C_{1-4}$ alkyl ethers thereof. Typical of these aminoplast resin intermediates are polymethylol derivatives, and their partial or complete ethers, of amides, such as urea, thiourea, guanidine and dicyandiamide. Particular examples of these condensates include dimethylolurea, tetramethylolurea, di(methoxymethyl)urea, dimethylol guanidine, trimethylol guanidine and dimethyloldicyandiamide.

Derivatives of substituted ureas can also be used, such as formaldehyde condensates, and their ethers, of ethyleneurea, methyleneurea, acetylenediurea, biuret, oxydimethyleneurea (uron) and iminodimethylencurea (triazone). Particular examples of these condensates include dimethylolethyleneurea, dimethylolmethyleneurea, tetramethylolacetylenediurea, trimethylolbiuret, di(methoxymethyl)uron and di(methoxymethyl)triazone.

Derivatives of triazines, such as of melamine, diaminotriazine, formoguanamine and 2-chloro-4,6-diaminotriazine, can also be used. These represent a preferred class of aminoplast resin intermediates. Specific examples include formaldehyde adducts such as di- and trimethylolmelamine, optionally partially methylated, hexamethoxymelamine, tetramethyloldiaminotriazine and tetramethylol-2-chloro-4,6-diaminotriazine.

Aminoplast resin intermediates also can be formed from diazines and azoles. Typical of these are formaldehyde adducts of 2,4-diamino-1,3-diazine, guanazole and diaminopyrrole.

As indicated above, nonionic wetting agents may be incorporated into the liquid compositions to accelerate the wetting of the cellulosic material. Such wetting agents include polyethylene oxides, such as a phenol or monohydric or polyhydric aliphatic alcohol which has been polyoxyethylated with ethylene oxide, for example, polyoxyethylated phenol. Such wetting agents usually comprise 0.01–0.15 weight % of the liquid composition.

Conveniently, the liquid compositions are prepared by forming solutions or emulsions of hydroxymethyl phosphorodiamidates or alkoxymethyl phosphorodiamidates in concentrated forms. This can be done by producing the hydroxymethyl- and alkoxymethylphosphorodiamidates in liquid carriers and then admixing therewith any other desired components prior to use of the mixtures as flame retardants. In many cases, the phosphorodiamidate simply can be stirred into a solvent medium containing formaldehyde, a sufficient amount of alkali metal hydroxide is then added and, after about 20 minutes at about 20°–30°C., the hydroxymethyl derivative is produced. In some cases, a solution of phosphorodiamidate in an organic solvent can be mixed with an aqueous medium containing the desired amount of formaldehyde, the expected total required amount of alkali metal hydroxide and, optionally, a dispersing agent. Subsequently, when needed, other desired components can be added to such concentrates to prepare liquid compositions which can carry the phosphorodimidate into cellulosic materials in the desired amount.

Any suitable method can be used to incorporate the liquid composition into the cellulosic material being treated. A sufficient amount of the composition should be applied to provide the desired amount of flame resistance. The amount of active ingredient, as above defined, should be 10–35 weight %, preferably 15–25%, of the weight of the dry cellulosic material being treated. The liquid composition can be applied as a squirted or air borne driven spray onto moving substrate. Preferably, the liquid composition or solution of active ingredient is applied, especially to fabrics, by a conventional padbath technique. Add-on or net pickup of solution usually is 60–200 weight %, preferably 80–120%, based on the weight of substrate.

Cellulosic fabrics which are treated with the compounds of this invention are soft and the imparted flame resistance is durable to laundering and any bleaching treatment which may accompany laundering. The effectiveness of the compounds of this invention is believed to be due to the combination of alkyl or haloalkyl and methylol groups (or their ethers) on the diamidate nitrogen atoms. When the compounds of this invention are used in combination with aminoplast resin precursors, only small amounts of the latter are required, thus ensuring substantial retention of the hand of the fabric being treated.

The compounds of this invention are particularly effective on all forms of cellulose which swell and become flexible upon exposure to the carrier solvent (water or organic solvent as described above) used to prepare the solution or liquid composition. When complete penetration of the cellulosic material is achieved by the treating solution, the flame resistance is imparted throughout the material. Suitable cellulosic materials include natural fibers, purified wood pulp and rayon. In the textile field, natural fibers include cotton, the preferred fiber, linen, viscose rayon, cuprammonium rayon, jute, hemp and ramie. Such materials can be treated in the form of raw fiber, carded stock, rovings, thread, yarn and felts as well as in the form of knitted and woven fabrics. Cellulosic materials which have been treated with the compounds of this invention are especially useful for tents, stage scenery, upholstery fabrics, slipcovers, draperies, wearing apparel for personnel in close relation to fire or heat, bedding, nightclothes, tarpaulins, insulation, padding, rope, string and twine.

In the following examples demonstrating the preparation and use of the compounds and compositions of this invention parts are by weight except where otherwise specified. Broad band proton decoupled P-31 NMR spectra are reported in ppm. relative to 85% phosphoric acid in the manner previously described. Fabrics are allowed a 24-hour exposure to room temperature and humidity prior to being evaluated for flame resistance. The terms hand, padding, laundering, limiting oxygen index (LOI), vertical flame test (VFT) and char length refer to the following:

Hand: the softness or a treated fabric relative to untreated fabric as the control. It is graded subjectively here on a scale of 1 to 5 in which 5 signifies a softness and flexibility virtually indistinguishable from the control while 1 signifies great stiffness relative to the control.

Padding: wetting the fabric with the phosphorodiamidate solution and then running the wet fabric between rollers to squeeze out liquid which is in excess of the desired pickup on the fabric.

Laundering, also expressed as home washing (HW): exposing the fabric to a standard laundering cycle, employing a washing solution of 100 grams of a commercial detergent ("Tide") per 15 gallons of water, and tumble drying the washed fabric.

Limiting Oxygen Index: determined with a 5-inch by 2-inch piece of fabric spread lengthwise in a vertical plane and supported along its vertical edges. The spread fabric is positioned inside a transparent circular (cylindrical) column open only at the top. The top of the column is one or more inches above the spread fabric. The interior of the column is provided with an upward flow, from its base, of a gaseous mixture of pure oxygen and pure nitrogen. The volume flow rate of each gas making up the mixture is instrumented and manually adjustable. To test fabric in this apparatus, the spread fabric is ignited from the top while gas mixture flows up the column. The flow rates of the nitrogen and oxygen are adjusted until the flame on the ignited fabric just goes out. The ratio of the volume flow of oxygen to the sum of the volume flows of oxygen and nitrogen is then calculated. This value, called the Limiting Oxygen Index (LOI), is the average of two determinations. As a standard of reference, untreated 8-oz. cotton twill used in the following examples to test the effectiveness of the compounds of this invention has an LOI value of 0.180±0.002 and is completely burned up in the vertical flame test. Hence, any treated cotton having an LOI value of greater than 0.180 is considered to exhibit some flame resistance. Air contains about 21 mole percent oxygen; therefore, fabrics with LOI values below about 0.210 can be expected to burn freely in a candlelike manner (from the top to the bottom) in air. For commercial applications, an LOI value of at least about 0.260–0.270 is considered acceptable.

Vertical Flame Test and Char Length: carried out in a 12-inch by 12-inch cabinet 30 inches high and having a glass front. Gas circulation is provided by a 4-inch high opening beneath the glass fron and a 6-inch diameter baffled hole at the top of the cabinet. It is provided with holder brackets on which a specimen holder is hung. The specimen holder provides a 1-inch wide by 14-inch high vertical open space and vertical side clips to hold edges of fabric which span this open space. Samples are ignited by a 6-inch Bunsen burner having a 0.375-inch inside diameter tube and a luminous flame 1.5 inches long. To conduct the test, a 2.75-inch by 10-inch fabric sample is held in the specimen holder by its vertical edges and the specimen holder is hung centrally by the holder brackets. The igniting flame is applied so that 0.75 inch of the lower end of the fabric is in the flame. This exposure is continued for 3.0 seconds and the flame is removed. After the flame has extinguished itself, the sample is removed from the holder. A hook with at attached weight is inserted into the sample on one side of the charred area 0.25 inch from the outside edge and 0.25 inch from the lower edge. For 2.0 to 6.0-oz. per square yard fabric, a 0.50-pound weight is used. The corner of the cloth at the opposite edge of the char from the load is gently raised until the sample and weight are clear of supporting surface. The length of the tear which occurs is measured (in inches) and reported below as char length. Where char length is reported below, it is understood to have been determined by this procedure and to be an average value of 2 or 4 determinations and neither or none of the samples burns the entire length. If any one sample burns the entire length (BEL), both or all samples are so rated.

EXAMPLE 1

2-Chloroethyl N-N'-Dimethylol-N,N'-dimethylphosphorodiamidate Preparation

162 Parts of 37% aqueous formaldehyde (2 moles) were cooled to 10°C. and adjusted to pH 10 with 30% aqueous sodium hydroxide. 186.6 Parts of 2-chloroethyl N,N'-dimethylphosphorodiamidate (1 mole) were added; additional sodium hydroxide was added simultaneously so as to maintain the pH of the reaction mixture at 7–10. The temperature was maintained at 10°C. Thirty minutes after completion of the addition, sodium hydroxide again was added to reestablish a pH of 10. After standing overnight at 20°–25°C. the pH was 7–8. The reaction mixture was vacuum distilled at 10–20 mm. pressure at 50°–65°C. until no further distillate was removed. The residual product was an extremely viscous, water soluble, oil. The P-31 NMR analysis of the product in water showed a multiplet of peaks centered at −16.4 ppm. This contrasted with the starting phosphorodiamidate which showed in water a multiplet centered at −21.0 ppm. Elemental analyses of the oil gave the following results. Calc'd. for $C_6H_{16}ClN_2O_4P$: C, 29.2; H, 6.5; Cl, 14.4; N, 11.4; P, 12.6. Found: C, 28.6; H, 6.0; Cl, 13.9; N, 10.8; P, 12.1.

EXAMPLE 2

Ethyl N,N'-Dimethylol-N,N'-dimethylphosphorodiamidate Preparation

The procedure of Example 1 was repeated except that 212 parts of ethyl N,N'-dimethylphosphorodiamidate (1 mole) were substituted for the diamidate shown. The P-31 NMR analysis of the product in dimethyl sulfoxide showed a multiplet of peaks centered at −16.1 ppm., in contrast with the starting phosphorodiamidate which showed a multiplet centered at 31 19.3 ppm. in dimethyl sulfoxide. Elemental analysis of the product, an oil gave the following results. Calc'd. for $C_6H_{17}N_2O_4P$: C, 34.0; H, 8.1; N, 13.2; P, 14.6. Found: C, 32.5; ; H, 7.1; N, 12.7; P, 13.6

EXAMPLE 3

3-Chloropropyl N,N'-Dimethylol-N,N'-dimethylphosphorodiamidate Preparation

Example 1 was repeated except that 260.6 parts of 3-chloropropyl N,N'-dimethylphosphorodiamidate were substituted for the diamdiate shown. The P-31 NMR analysis of the product in water showed a multiplet centered at −16.7 ppm., in contrast with the starting phosphorodiamidate which showed in water a multiplet centered at −21.0 ppm. Elemental analyses of the product gave the following results. Calc'd. for $C_7H_{18}ClN_2O_4P$: C, 32.3; H, 7.0; Cl, 13.6; N, 10.8; P, 11.9. Found: C, 32.9; H, 6.7; Cl, 13.5; N, 10.6; P, 12.8.

EXAMPLE 4

1,3-Dichloro-2-propyl N,N'-Dimethylol-N,N'-dimethylphosphorodiamidate Preparation Example 1 was repeated except that 295 parts of 1,3-dichloro-2-propyl N,N'-dimethylphosphorodiamidate were substituted for the diamidate shown. The P-31 NMR analysis of the product in a chloroform-hexafluorobenzene mixture showed a multiplet centered at −16.4 ppm., in contrast with the starting phosphorodiamidate which showed in a benzenechloroform mixture a multiplet centered at −19.4 ppm. Elemental analyses of the product gave the following results. Calc'd. for $C_7H_{17}Cl_2N_2O_4P$: C, 28.5; H, b 5.8; Cl, 24.0; N, 9.5; P, 10.5. Found: C, 28.3; H, 5.2; Cl, 23.6; N, 9.5; P, 10.1.

EXAMPLE 5

2,2,2-Trichloroethyl N,N'-Dimethylol-N,N'-dimethylphosphorodiamidate Preparation Example 1 was repeated except that 255.4 parts of 2,2,2-trichloroethyl N,N'-dimethylphosphorodiamidate were substituted for the diamidate shown. The P-31 NMR analysis of the product in a chloroform-hexafluorobenzene mixture showed a broad multiplet centered at −16.5 ppm., in contrast with the starting phosphorodiamidate which showed in chloroform a multiplet centered at −19.0 ppm. Elemental analyses of the product gave the following results. Calc'd. for $C_6H_{14}Cl_3N_2O_4P$: C, 22.8; H, 4.5; Cl, 33.7; N, 8.9; P, 9.8. Found: C, 23.0; H, 4.1; Cl, 32.6; N, 8.7; P, 7.6.

EXAMPLE 6

2-Chloroethyl N,N'-Dimethylol-N,N'-trimethylenephosphorodiamidate Preparation

A solution of 395 parts (2 moles) of 2-chloroethyl phosphoric dichloride in 533 parts of methylene dichloride was added to a solution, held at 0°C., of 148 parts (2 moles) of 1,3-diaminopropane and 404 parts (4 moles) of triethylamine in 4,000 parts of methylene dichloride. The mixture was allowed to warm to 20°C.

overnight, then to 40°C., and filtered to remove solid triethylamine hydrochloride. The filtrate was vacuum distilled at 100 mm. Hg at up to 50°C. until no further distillate was removed. The recovered solid 2-chloroethyl N,N'-trimethylenephosphorodiamidate was submitted to elemental analyses with the following results. Calc'd. for $C_5H_{12}ClN_2O_2P$: C, 30.2; H, 6.2; N, 14.1; P, 15.6. Found: C, 30.5; H, 5.8; N, 13.8; P, 15.2. The product in water showed a single P-31 NMR peak at −15.8 ppm.; its molecular weight was confirmed by high resolution mass spectrometry. 19 Parts of the cyclic diamidate were dissolved in 17 parts of 37% aqueous formaldehyde. 30% Aqueous sodium hydroxide was added at 20°C. to produce a pH of 10, and the solution was allowed to stand overnight. The P-31 NMR analysis of the product in water showed a multiplet of peak centered at −12.7 ppm., confirming that it was the desired compound.

EXAMPLE 7

Treatment of Cotton Fabric with Alkyl N,N'-Dimethylol-N,N'-dimethylphosphorodiamidates and Aminoplast resin of the alkyl N,N'-dimethylol-N,N'-dimethylphosphorodiamidate. A char length of ≦ 7.0 inches is considered passable and is so indicated in the table. Greater char lengths are designated as failing.

TABLE 2

| Alkyl Group | Wt. % Add-On Nominal | Wt. % Add-On Analysis | Durability After 40 Home Washes | Char Length Initial | Char Length After 40 Home Washes | LOI Initial | LOI After 40 Home Washes |
|---|---|---|---|---|---|---|---|
| ClCH₂CH₂ | 12.5 | 10.7 | 66% | Pass | Fail | .257 | .246 |
| ClCH₂CH₂ | 15.0 | 11.5 | 70% | Pass | Fail | .260 | .255 |
| ClCH₂CH₂ | 17.5 | 15.2 | 73% | Pass | Pass | .270 | .259 |
| ClCH₂CH₂ | 20.0 | 17.3 | 59% | Pass | Pass | .274 | .255 |
| ClCH₂CH₂CH₂ | 12.5 | 13.0 | 63% | Fail | Fail | .267 | .251 |
| ClCH₂CH₂CH₂ | 15.0 | 15.9 | 60% | Pass | Pass | .274 | .257 |
| ClCH₂CH₂CH₂ | 17.5 | 18.0 | 63% | Pass | Pass | .283 | .274 |
| ClCH₂CH₂CH₂ | 20.0 | 19.8 | 61% | Pass | Pass | .288 | .278 |
| CH₃CH₂ | 12.5 | — | — | Pass | Fail | .267 | — |
| CH₃CH₂ | 15.0 | — | — | Pass | Pass | .256 | — |
| CH₃CH₂ | 17.5 | — | — | Pass | Pass | .271 | — |
| CH₃CH₂ | 20.0 | — | — | Pass | Pass | .271 | — |
| (ClCH₂)₂CH | 12.5 | 12.4 | 78% | Fail | Fail | .279 | — |
| (ClCH₂)₂CH | 15.0 | 16.6 | 67% | Pass | Fail | .276 | — |
| (ClCH₂)₂CH | 17.5 | 18.8 | 65% | Pass | Fail | .293 | — |
| (ClCH₂)₂CH | 20.0 | 20.7 | 68% | Pass | Pass | .287 | — |

Sixteen aqueous padbaths were prepared, each containing per 100 parts of solution, 8 parts of trimethylolmelamine, 2 parts of ammonium chloride and the number of parts shown in Table 2 of an alkyl N,N'-dimethylol-N,N'-dimethylphosphorodiamidate. The baths were padded onto 4-oz. cotton flannelette samples to 100% pickup. The impregnated fabrics were dried for 10 minutes at 100°C., cured for 4 minutes at 165°C., subjected to home washes and tumble-dried. Elemental analyses were carried out to determine add-ons of the phosphorodiamidates initially and after 40 home washes. In all cases, the nitrogen/phosphorus ratios, corrected for the nitrogen content due to aminoplast resin, were substantially constant. The following table shows the results of the evaluations of the treated fabric samples. Durability refers to the % phosphorodiamidate retained on the fabric after 40 home washes. The alkyl groups shown in the table refer to the alkyl moiety

EXAMPLE 8

Treatment of Cotton Fabric with 2-Chloroethyl N,N'-Dimethylol-N,N'-dimethylphosphorodiamidate and Trimethylolmelamine Three aqueous padbaths were prepared and designated A, B and C, each containing, per 100 parts of solution, 8 parts of trimethylolmelamine, 2 parts of ammonium chloride (curing agents), and 10, 15 and 20 parts, respectively, of 2-chloroethyl N,N'-dimethylol-N,N'-dimethylphoshorodiamidate. The baths were padded onto 8-oz. cotton twill fabric samples (correspondingly designated A, B and C) to 100% pickup. The impregnated fabrics were dried for 10 minutes at 100°C., cured for 4 minutes at 165°C., subjected to home washes and tumble-dried. Elemental analyses were carried out to determine add-ons of the phosphorodiamidate. Table 3 shows the results of the evaluations of the treated fabrics.

TABLE 3

| Sample | Wt. % Add-On Initial | Wt. % Add-On After 10 Home Washes | Durability After 10 Home Washes | Atomic Cl/P Ratio Initial | Atomic Cl/P Ratio After 10 Home Washes | Char Length (inches) Initial | Char Length (inches) After 10 Home Washes | LOI Initial | LOI After 10 Home Washes |
|---|---|---|---|---|---|---|---|---|---|
| A | 9.6 | 7.0 | 73% | 1.04 | 0.96 | 4.25 | 6.63 | .260 | .257 |
| B | 14.0 | 10.8 | 78% | 1.13 | 1.00 | 4.88 | 4.75 | .285 | .274 |
| C | 19.2 | 14.4 | 75% | 1.12 | 0.98 | 3.75 | 4.25 | .300 | .284 |

EXAMPLE 9

Treatment of Cotton Fabric with 2-Chloroethyl N,N'-Dimethylol-N,N'-Trimethylenephosphorodiamidate and Trimethylolmelamine Two aqueous padbaths were prepared and designated A and B, each containing, per 100 parts of solution, 16 parts of trimethylolmelamine, 1 part of 2-methyl-2-aminopropanol-1 hydrochloride (curing agent) and 31 and 41.3 parts, respectively, of 2-chloroethyl N,N'-dimethylol-N,N'-trimethylenephosphorodiamidate. The pH of the padbaths was 6.5. Padding, drying, curing and evaluation were carried out as in Example 8. Table 4 shows the results of the evaluation of the treated fabrics.

TABLE 4

| Wt. % Add-On of P | A | B |
|---|---|---|
| as dried | 1.54 | 1.89 |
| post cure prewash | 1.54 | 1.85 |
| after 1 home wash | 1.52 | 1.90 |
| after 10 home washes | 1.53 | 1.86 |
| Wt. % Add-On of N | | |
| as dried | 6.50 | 6.46 |
| post cure prewash | 6.61 | 6.67 |
| after 1 home wash | 5.74 | 5.98 |
| after 10 home washes | 5.84 | 6.17 |
| LOI | | |
| as dried | 0.289 | 0.276 |
| post cure prewash | 0.279 | 0.274 |
| after 1 home wash | 0.319 | 0.329 |
| after 10 home washes | 0.324 | 0.330 |

Example 10

Treatment of Cotton Fabric with 2-Chloroethyl N,N'-Dimethylol-N,N'-Dimethylphosphorodiamidate Four aqueous padbaths were prepared so that each contained, per 100 parts of solution, 1 part of 2-methyl-2-aminopropanol-1 hydrochloride (curing agent) and either 15 or 20 parts of 2-chloroethyl N,N'-dimethylol-N,N'-dimethylphosphorodiamidate (DDPDA). To each of two of the baths also were added 6 parts of trimethylolmelamine (TMM). The baths were padded onto 5-oz. cotton flannelette samples to 120% pickup, then dried, cured and evaluated as in previous examples. Table 5 shows the results of the evaluation of the treated fabrics. The table also shows the results of the evaluation of fabrics padded with four other padbaths in which 2-chloroethyl N,N'-dimethylphosphorodiamidate (DPDA) was used in place of DDPDA. Char length was obtained by employing a three second ignition and using the longer of the two tear lengths from two determinations. Durability refers to the % of the element (P, N or Cl) retained on the fabric after 10 home washes.

TABLE 5

| Parts in Bath | | Initial Wt. % Add-On | % Loss on Curing | LOI | | Char Length | | Durability After 10 Home Washes | | |
|---|---|---|---|---|---|---|---|---|---|---|
| DDPDA | TMM | DDPDA | | Initial | After 10 Home Washes | Initial | After 10 Home Washes | P | N | Cl |
| 15 | 0 | 18.2 | 0 | .236 | .221 | BEL | BEL | 67 | 69 | 57 |
| 20 | 0 | 23.6 | 0 | .261 | .230 | 4.75 | BEL | 66 | 64 | 55 |
| 15 | 6 | 18.9 | 0 | .279 | .261 | 3.25 | 2.75 | 85 | 96 | 81 |
| 20 | 6 | 24.4 | 0 | .285 | .271 | 3.25 | 2.5 | 80 | 91 | 68 |
| DPDA | TMM | DPDA | | | | | | | | |
| 15 | 0 | 12.2 | 32 | .247 | .196 | BEL | BEL | 63 | 33 | 11 |
| 20 | 0 | 17.9 | 25 | .277 | .213 | 2.75 | BEL | 61 | 39 | 11 |
| 15 | 6 | 16.9 | 6 | .291 | .229 | 2.75 | BEL | 53 | 58 | 16 |
| 20 | 6 | 20.7 | 14 | .312 | .245 | 2.75 | BEL | 61 | 52 | 15 |

It can be seen that the DDPDA is superior in durability to DPDA. The superior durability and the improved hydrolytic stability of the bound halogen in DDPDA are believed due to the complete substitution of the diamidate nitrogens. It should be further noted that DDPDA is more completely used than DPDA, thereby avoiding waste of the material with attendant coating of equipment.

EXAMPLE 11

2,2-Bis(Bromomethyl)-3-Bromopropyl-N,N'-Dimethylol-N,N'-Dimethylphosphorodiamidate A. A mixture of tribromoneopentyl alcohol (150 g., 0.467 mole), potassium chloride (0.3 g.) and phosphorous oxychloride (200 ml.; 2.1 moles) was stirred at reflux (105°–110°C.) for about 2 hours (until evolution of hydrogen chloride ceased). The reaction mixture was allowed to cool to room temperature and stand overnight under nitrogen atmosphere. Unreacted phosphorous oxychloride was removed by distilling at 25 mm. of Hg., leaving an orange brown oil (208 g.) ($n_D^{25}$ 1.5513) whose composition as 2,2-bis(bromomethyl)-3-bromopropylphosphorodichloridate was confirmed by P-31 and proton NMR spectra.

B. A solution of 2,2-bis(bromomethyl)-3-bromopropylphosphorodichloridate (100 g.) in methylene chloride (500 ml.) was treated with 4 molar equivalents of methylamine at 0° to 10°C. Methylamine hydrochloride precipitated and was removed by filtration and the solution was washed with three 50 ml. portions of water and dried over anhydrous sodium sulfate. Removal of the methylene chloride under reduced pressure yielded a pale yellow oil (88 g.) which when triturated with water provided a solid which when recrystallized from n-butyl chloride melted at 68.0°–69.5°C. The solid was confirmed to be $(BrCH_2)_3CCH_2OP(O)(NHCH_3)_2 \cdot H_2O$. Calc'd. for $C_7H_{18}Br_3N_2O_3P$: C, 18.7; H, 4.0; P, 6.2%. Found: C, 18.4; H, 3.9; P, 6.0%.

C. A mixture of 2,2-bis(bromomethyl)-3-bromopropyl-N,N'-dimethylphosphorodiamidate hydrate (40 g.; 0.089 mole), 37% formaldehyde (15.1 g; 0.188 mole) and isopropyl alcohol (8.9 g.) was heated on a steam bath until a soluton was obtained. The pH of the solution was adjusted to 9.5 with aqueous NaOH and the solution was allowed to stand overnight at room temperature; after standing overnight the pH was 8.5. The isopropyl alcohol, water and unreacted formaldehyde were removed by distillation at 25 mm. of Hg. The residue was 2,2-bis(bromomethyl)-3-bromopropyl-N,N'-dimethylol-N,N'-dimethylphosphorodiamidate (P-31 NMR in isopropanol/water as exhibited a 1.0/5.7/8.2 ratio of singlets at −20.3 ppm). The compound was miscible with a 75/25 (by volume) mixture of water and isopropanol and the resulting solution was stable for at least one month.

EXAMPLE 12

Use of
2,2-Bis(Bromomethyl)-3-Bromopropyl-N,N'-Dimethylol-N,N'-Dimethylphosphorodiamidate
(Dimethylolated in situ)

10 G., for a 10% flame retardant padbath, or 20g., for 20% padbath, of 2,2-bis(bromomethyl)-3-bromopropyl-N,N'-dimethylphosphorodiamidate, 10 g. of isopropanol and 8 g. of 37% aqueous formaldehyde were mixed and the pH of the mixture was adjusted to 11 with 15% aqueous sodium hydroxide. The mixture was stirred at room temperature for about 1 hour, with pH adjustment to 10–11 when necessary. 24 G. of 25% aqueous trimethylolmelamine was then added and the pH was adjusted to 7–8 with hydrochloric acid. 2 G. of 2-methyl-2-aminopropanol-1 hydrochloride (catalyst) were dissolved in the solution and pieces of 4 oz. cotton flannelette fabric were immediately padded with the solution. The wet pickup of the padding solution was 100–120%, based on weight of fabric. The treated fabrics were dried for 10 minutes at 100°C. and then cured for four minutes at 160°–165°C. The results of LOI and VFT tests and the durability to home washes in terms of phosphorus in the fabric are summarized in Table 6.

TABLE 6

| I. | Flame Retardant (%) in Padbath | 10 | 20 |
|---|---|---|---|
| II. | Durability Tests | | |
| | wt. % P on fabric after cure | 0.82 | 1.26 |
| | wt. % P on fabric after 10 home washes (HW) | 0.63 | 1.06 |
| | % retained after 10 HW | 77 | 84 |
| III. | Flame Retardancy Tests | | |
| | A. LOI | | |
| | 1. initial (after cure) | .255 | .302 |
| | 2. after 10 HW | .234 | .258 |
| | B. VFT (char length, in.) | | |
| | 1. initial (after cure) | 3 | 3 |
| | 2. after 10 HW | 3 | 3 |

In the above table, the wt. % of P on fabric of 0.82 and 1.26 correspond to 11.4% and 17.5% of the flame retardant, as $(BrCH_2)_3CCH_2OPO(NHCH_3)_2$ (that is, as unmethylolated compound, on fabric. The treated fabrics had soft hand. The above results show that the flame retardant compounds of the present invention provide durable and effective flame retardancy to cotton flannelette.

EXAMPLE 13

2,3-Dibromopropyl-N,N'-Dimethylol-N,N'-Dimethylphosphorodiamidate 1,340 G. (8.73 moles) of phosphorus oxychloride were added to 436 g. (2.0 moles) of 2,3-dibromopropyl alcohol containing 1 g. of potassium chloride and the mixture was refluxed for 3 hours; HCl evolution had then ceased. The mixture was vacuum stripped down to a pressure of 5 mm. of Hg. at 90°C. 318 G. of the residue, 2,3-dibromopropylphosphorodichloridate, were diluted in 2 liters of methylene cloride and 118 g. (3.8 moles) of methylamine were bubbled in while maintaining the temperature below 0°C. After 2 hrs., the reaction product was vacuum stripped to 5 mm. of Hg. at 90°C. The product, a dark orange oil, was washed with 500 g. of water at 50°C. and dried.

10 G of this product as a 50% solution in isopropyl alcohol were stirred into 2 molar equivalents of aqueous formaldehyde, adjusted to pH 10.5 with 15% aqueous NaOH and allowed to stand 1 hour at 25°C. The resulting solution was adjusted to pH 7 with aqueous HCl. 12 G. of trimethylolmelamine were dissolved in the solution, followed by 0.5 of 2-methyl-2-aminopropanol-1 hydrochloride and the bath was made up with water to 50 g. The bath was padded on 4 oz. cotton flannel to an add-on of 10% of the phosphorodiamidate and 12% of the resin, dried at 115°C. for 6 minutes and cured at 165°C. for 4 minutes. The cured flannel after 14 hours of detergent washing (deemed equivalent to 10 home washes) gave a char length in the vertical flame test of 1.8 inches.

EXAMPLE 14

2,2-Bis(Bromomethyl)-3-Bronopropyl-N,N'-Dimethylol-N,N'-Trimethylenephosphorodiamidate 1,340 G. (8.73 moles) of phosphorus oxychloride were added to 650 g. (2.0 moles) of tribromoneopentyl alcohol and 1 g. of KCl and the mixture was refluxed until HCl evolution ceased (3 hrs.). The resulting mixture containing tribromoneopentyl phosphorodichloridate was vacuum stripped down to 5 mm. of Hg. at 90°C., leaving an orange brown oil characterized by P-31 NMR in chloroform by a single peak at + 2.01 ppm.

449.2 G. of tribromoneopentyl phosphorodichloridate were added to a solution at 0 to −10°C. of 74 g. of 1,3-diaminopropane and 202 g. of triethylamine in 1,200 g. of methylene chloride. After standing 1 hour the mass was washed with 1,200 g. of water at 30°C. The organic phase was vacuum stripped to 5 mm. of Hg, at 90°C. By P-31 NMR analysis, the product showed a major peak in 50/50 methanol/water (by volume) at −13.5 ppm. and a minor peak at −17.3 ppm. (expected of substantially pure 2,2-bis(bromomethyl)-3-bromopropyl-N,N-trimethylenephosphorodiamidate).

This product was made into padbaths by adding a 60% solution of it in 50/50 water/isopropanol (by volume) to 2 molar equivalents of 37% aqueous formaldehyde, adding 15% aqueous NaOH to pH 10.5, allowing the mixture to stand 1 hour at 25°C., neutralizing the mixture with 10% aqueous HCl, dissolving trimethylolmelamine in the mixture and, after adding 1%, based on the bath weight, of 2-methyl-2-aminopropanol-1 hydrochloride, making the bath up to weight with water. The baths were padded at 100% pickup on 4 oz. cotton flannelette, dried 10 minutes at 115°C. and cured 4 minutes at 165°C.

The treated fabrics were analyzed for N and P and tested by LOI and VFT as initially cured and after 10 home washes (HW). Results are given in Table 7.

TABLE 7

| Wt. % Pad Bath Components | Run Designation A | B | C |
|---|---|---|---|
| % of phosphorodiamidate | 10 | 15 | 20 |
| % of 37% aq. formaldehyde | 8 | 8 | 8 |
| % of trimethylolmelamine | 6 | 6 | 6 |
| % P in Fabric | | | |
| initial | 0.66 | 1.02 | 1.24 |
| after 10 HW | 0.62 | 0.87 | 0.93 |
| % N in fabric | | | |
| initial | 4.07 | 4.04 | 4.20 |
| after 10 HW | 3.73 | 3.83 | 3.54 |
| LOI | | | |
| initial | .261 | .283 | .293 |
| after 10HW | .244 | .258 | .258 |
| VFT (char length, in.) | | | |
| initial | 3 | 2.75 | 3.5 |

TABLE 7-continued

| Wt. % Pad Bath Components | Run Designation A | B | C |
|---|---|---|---|
| after 10 HW | 2.25 | 3 | 2 |

EXAMPLE 15

Methylolated 2,2-Bis(Bromomethyl)-3-Bromopropyl-N,N'-Dimethylphosphorodiamidate in Combination with Resin 44.9 Parts of 2,2-bis(bromomethyl)-3-bromopropyl-N,N'-dimethylphosphorodiamidate, 41.3 parts of poly-(oxyethylene) ether of molecular weight 350 and 9.8 parts of 37.4% aqueous formaldehyde were mixed and warmed to 60°C. to produce a clear solution; the solution was cooled and filtered to remove trace haze. A P-31 NMR spectrum of the solution showed a small peak at −19.5 ppm. (believed to be unreacted starting phosphorodiamidate), a doublet at −18.4 and −17.8 ppm. and multiple absorption at −16.8, −16.4 −16.2 and −15.7 ppm. A sample of this concentrate afforded the same spectrum after standing at room temperature for 9 weeks.

In separate vessels, according to formulation, trimethylolmelamine was dissolved in boiling water to produce clear solutions. 4%, Final bath weight basis, of the sodium salt of the monoester of sulfuric acid and a mixture of $C_{12-18}$ fatty alcohols were dissolved in the solutions; appropriate amounts of the above phosphorodiamidate concentrate were then added. Just prior to use 1%, final bath weight basis, of 2-methyl-2-aminopropanol-1 hydrochloride was dissolved in the cooled solutions. 4Oz. cotton flannel fabrics were padded in the vessels to 100% solution pickup, dried at 120°C. for 3 minutes and then cured for 3 minutes, one piece from each vessel at 165°C. another piece from each vessel at 180°C. The fabrics were home washed 14 times and then tested for hand and char length by VFT.

Varied bath components used and the char length (in inches) by VFT and hand after 14 home washes are shown in Table 8. Hand, as reported in the table, was determined qualitatively based on a scale in the order soft (S), good (G), fair (F), harsh (H) and poor (P).

TABLE 8

| Varied Bath Components, wt.% | | Cure Temp (°C.) | VFT (char in in.) | | Hand |
|---|---|---|---|---|---|
| FR(a) | TMM(b) | | Initial | 14 HW | |
| 8 | 20 | 165 | 2.7 | 2.2 | H |
| 8 | 20 | 180 | 2.3 | 2.5 | H |
| 10 | 18 | 165 | 2.0 | 1.9 | H |
| 10 | 18 | 180 | 1.8 | 2.4 | H |
| 12 | 14 | 165 | 2.3 | 3.0 | F |
| 12 | 14 | 180 | 2.3 | 2.5 | F |
| 15 | 10 | 165 | 1.4 | 2.5 | S |
| 15 | 10 | 180 | 1.6 | 3.2 | S |
| 15 | 12 | 165 | 2.2 | 3.2 | G |
| 15 | 12 | 180 | 1.7 | 3.7 | G |

(a): $(BrCH_2)_3CCH_2OP(NHCH_3)_2 \cdot 1.23CH_2O$ (with =O on P)

(b): Trimethylolmelamine

It can be seen that the combination of 10–14 weight percent resin and 12–15 weight percent diamidate provides improvement in the hand of the cotton flannel without significant change of flame retardancy.

I claim:

1. Alkyl phosphorodiamidate having the formula

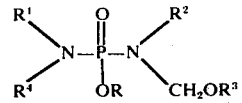

wherein
R is $C_{1-5}$ alkyl having 0–3 substituents selected from chloro and bromo,
$R^3$ is H or $C_{1-4}$ alkyl,
$R^4$ is H or $CH_2OR^5$ wherein $R^5$ is H or $C_{1-4}$ alkyl, and
$R^1$ and $R^2$ conjointly is $C_{2-5}$ alkylene, provided that all carbon atoms alpha to the amide nitrogen and ester oxygen atoms are free of halo substituents.

2. Phosphorodiamidate of claim 1 wherein R is $C_{2-5}$ haloalkyl having 1–3 bromo substituents.

3. Phosphorodiamidate of claim 1 wherein R is 2,2-bis(bromomethyl)-3-bromopropyl, $R^1$ and $R^2$ taken conjointly is 1,3-propylene, $R^3$ is H and $R^4$ is H or $CH_2OH$.

4. Phosphorodiamidate of claim 1 wherein R is 2-chloroethyl, $R^3$ is H, $R^4$ is $CH_2OR^5$ wherein $R^5$ is H and $R^1$ and $R^2$ conjointly is 1,3-propylene.

* * * * *